US011241587B2

(12) United States Patent
Lilge et al.

(10) Patent No.: US 11,241,587 B2
(45) Date of Patent: Feb. 8, 2022

(54) FIBER OPTIC LIGHT DELIVERY, MONITORING AND APPARATUS THEREFOR

(71) Applicants: Theralase Technologies, Inc., Toronto (CA); University Health Network, Toronto (CA)

(72) Inventors: Lothar Lilge, Toronto (CA); Arkady Mandel, Toronto (CA); Wayne Embree, Toronto (CA); Don Lem, Toronto (CA); Jenny Wu, Toronto (CA); Roger Dumoulin-White, Toronto (CA)

(73) Assignees: Theralase Technologies, Inc., Toronto (CA); University Health Network, Toronto (CA)

( * ) Notice: Subject to any disclaimer, the term of this patent is extended or adjusted under 35 U.S.C. 154(b) by 642 days.

(21) Appl. No.: 15/289,574

(22) Filed: Oct. 10, 2016

(65) Prior Publication Data
US 2017/0100606 A1   Apr. 13, 2017

Related U.S. Application Data

(60) Provisional application No. 62/238,958, filed on Oct. 8, 2015.

(51) Int. Cl.
*A61N 5/06* (2006.01)
*A61B 5/20* (2006.01)
*A61B 90/30* (2016.01)
*A61B 5/00* (2006.01)
*A61M 25/00* (2006.01)

(52) U.S. Cl.
CPC ............ *A61N 5/062* (2013.01); *A61B 5/0084* (2013.01); *A61B 5/202* (2013.01); *A61B 5/4839* (2013.01);
(Continued)

(58) Field of Classification Search
CPC . A61B 2090/306; A61B 5/0084; A61B 5/202; A61B 5/4839; A61B 5/6858;
(Continued)

(56) References Cited

U.S. PATENT DOCUMENTS

| 5,125,925 A | 6/1992 | Lundahl |
| 5,292,320 A | 3/1994 | Brown et al. |

(Continued)

OTHER PUBLICATIONS

Abstract of Van Staveren et al., "Integrating sphere effect in whole-bladder-wall photodynamic therapy: III. Fluence multiplication, optical penetration and light distribution with an eccentric source for human bladder optical properties." Physics in medicine and biology 41.4 (1996).

(Continued)

*Primary Examiner* — Michael W Kahelin
*Assistant Examiner* — Vynn V Huh
(74) *Attorney, Agent, or Firm* — Caesar Rivise, PC (57) ABSTRACT

Apparatus for illuminating comprises one or more fibers, the one or more fibers including fiber portions meeting at an apex and a bottom location to form a three dimensional cage; a detector attached to each of the fiber portions for receiving light and transmitting light along each of the fiber portions, respectively; and an illumination member situated within the cage. A method for illuminating a hollow member includes the steps of inserting one or more fibers into the hollow member, wherein one or more fibers include fiber portions that meet at a location to form a three-dimensional cage; permitting light to emit from within the three-dimensional cage and towards the fiber portions; receiving light at distinct locations on each of said fibers; and allowing each of the fibers to transmit the light received on each of the fiber portions out of the hollow member.

19 Claims, 10 Drawing Sheets

(52) U.S. Cl.
CPC ............ *A61B 5/6858* (2013.01); *A61B 90/30* (2016.02); *A61M 25/0074* (2013.01); *A61B 2090/306* (2016.02); *A61M 2205/3306* (2013.01); *A61M 2210/1085* (2013.01); *A61N 2005/061* (2013.01); *A61N 2005/063* (2013.01)

(58) Field of Classification Search
CPC ............ A61B 90/30; A61B 18/20–28; A61M 2205/3306; A61M 2210/1085; A61M 25/0074; A61N 2005/061; A61N 2005/063; A61N 5/062; A61N 5/06–2005/073
USPC ...................................... 606/2–19; 607/88–94
See application file for complete search history.

(56) References Cited

U.S. PATENT DOCUMENTS

| | | | |
|---|---|---|---|
| 2001/0056278 A1* | 12/2001 | Nield | A61B 18/22 606/15 |
| 2005/0075704 A1* | 4/2005 | Tu | A61N 5/062 607/88 |
| 2006/0195165 A1 | 8/2006 | Gertner et al. | |
| 2008/0129993 A1* | 6/2008 | Brennan | A61B 5/0075 356/301 |

OTHER PUBLICATIONS

International Search Report for related PCT/IB2016/056061 dated Jan. 3, 2017.

* cited by examiner

FIBER OPTIC LIGHT DELIVERY, MONITORING AND APPARATUS THEREFOR

FIELD OF THE INVENTION

The present invention relates to the delivery and monitoring of light within a body cavity. In particular, a method and apparatus are disclosed for providing light within a body cavity and/or hollow organ, such as a bladder or lung or other organ and for monitoring the irradiance, fluence or fluence rate within that body cavity and/or hollow organ from a single or multiple locations, during single or multiple procedures.

BACKGROUND OF THE INVENTION

Photo Dynamic Therapy ("PDT") is currently an active area of research for the treatment of diseases associated with unwanted and/or hyper-proliferating cells such as cancer and non-malignant lesions. PDT involves the use of one (1) or more Photo Dynamic Compounds ("PDCs") and/or Photo-Sensitizers ("PSs") and/or formulations thereof used in conjunction with other compounds and/or other chemicals (herein "PSs") delivered to a patient by various means, topically, intravenously, inhalation, intraperitoneally and/or intravesically, among others; wherein the PSs are activated when exposed to light to induce damage to a cell or tissue (e.g. cellular damage or damage via vascular acting photo sensitizers). PDT has been applied in various conditions including hollow organs such as the bladder. In the case of a hollow organ such as the bladder, a light source is inserted into the bladder via the urethra, and the internal wall of the bladder, which has been treated with one or more PSs is exposed to the light. U.S. Pat. No. 5,125,925 proposes a fiber optic light source and single sensing optical fibers inserted into the bladder that senses light at its tip or along its length at any sensor and/or detector location. All references are incorporated herein by reference.

SUMMARY OF THE INVENTION

Apparatus for illuminating comprises one or more fibers, the one or more fibers including fiber portions meeting at an apex and a bottom location to form a three dimensional cage; a detector attached to each of the fiber portions for receiving light and transmitting light along each of the fiber portions, respectively; and an illumination member situated within the cage. A method for illuminating a hollow member includes the steps of inserting one or more fibers into the hollow member, wherein one or more fibers include fiber portions that meet at a location to form a three-dimensional cage; permitting light to emit from within the three-dimensional cage and towards the fiber portions; receiving light at distinct locations on each of said fibers; and allowing each of the fibers to transmit the light received on each of the fiber portions out of the hollow member.

OVERVIEW

The stages of bladder cancer predominately follow a progression from Carcinoma in Situ ("CIS"), through to Ta or T1, known as Non-Muscle Invasive Bladder Cancer ("NMIBC") through to T2 and T3, known as Muscle Invasive Bladder Cancer ("MIBC") and finally T4, in which the cancer has spread from the bladder and has metastasized outside of the bladder. Bladder cancer, once metastasized, can become life threatening; therefore, it is important to limit the spread of the disease and destroy NMIBC and/or MIBC before it has metastasized.

A bladder lesion (or tumor) may be located on the wall of the bladder. In PDT, the goal is to cause a PS to be absorbed or attached to the bladder tumor cells. To accomplish this objective, a catheter is inserted through the patient's urethra and a certain dose of a PS is instilled into the bladder. The larger the bladder, the greater the amount of drug in solvent that is inserted into the bladder. Furthermore, the larger the size of the bladder, the greater the surface area of the bladder; thus, it is desirable to have a homogeneous distribution of the drug throughout the bladder. In an exemplary embodiment of the present invention, the invention may be used in combination with a PS such as TLD-1433. In further embodiments of the device, the device may beused without a PS and be used to deliver light only to the target, such as inflamed bladder tissues delivered with Low Level Laser Therapy ("LLLT").

Again, TLD-1433 is merely exemplary, as other photo sensitizers may also be used (including, for example, vascular acting photosensitizers).

The above explanation is exemplary with regard to PDT. It is understood that other therapies may also be used, including low-level laser therapy (LLLT).

The above explanation is with regards to a photo sensitizer. To clarify, a photo sensitizer is a molecule that produces a chemical change in another molecule in a photochemical process.

After the PS has been instilled into the bladder, the drug is activated by a light source. It is desirable to have a homogeneous distribution of light within the bladder to uniformly activate the PS. Theoretically, it would be desirable to drain the PS from the bladder, fill the bladder, with distilled water, insert a light emitter into the bladder, and activate the light source. While theoretically such a procedure is desirable, in actuality, such a procedure may not work safely or effectively because the bladder is not a perfect sphere. Bladders come in many shapes, and sizes, with unique geometrical features all to themselves, lending to different anatomical configurations. Therefore, the amount of light that is deposited onto a bladder wall surface from a light emitter may vary significantly. There may be hotspots (excessive irradiation) and cold spots (insufficient irradiation) leading to variations in the activation of the PS and hence ability of the PS to destroy cancerous tissue. As a result, over activation of a PS in some areas is possible. In other areas, under activation of the PS may occur. In further areas, the PS may not be activated at all.

In one exemplary embodiment of the present invention, a light emitter and twelve (12) optical sensors, able to detect irradiance, fluence or fluence rate, are inserted into a bladder. The combination of the emitter and optical sensors (along with optical fibers to which the sensors are attached) typically is inserted through a channel of very small size, for example, 4.5 mm (13.5 French) in diameter, in the case of a rigid cystoscope and 2.5 mm (7.5 French) in diameter for a flexible cystoscope. The emitter and the optical fibers may be placed through the working channel of the cystoscope, inserted through the urethra of a patient and upon entering the bladder opened up like an umbrella. In this manner, it is possible to place the various detectors at strategic locations around the bladder wall, and thus compare the irradiance level at up to twelve (12) locations within the bladder.

The detectors described herein are for measuring irradiance. It is understood that this is merely exemplary as other measurement, such as fluence rate, may be included.

Because light is illuminating in a confined location, such as a bladder, the bladder may act like an integrating sphere. Thus, light will be reflected off the surface of the bladder and become incident onto another location of the bladder wall, from which it will be reflected again. Depending on the amount of reflected light, which varies according to the albedo (degree of "whiteness" or reflection coefficient), which may significantly affect the amount of light within a bladder at any particular location. This effect is known as the multiplication factor for integrating spheres and has been demonstrated to be between 2 and 6 for the human bladder)
Reference:
Integrating sphere effect in whole-bladder wall photodynamic therapy: III. Fluence multiplication, optical penetration and light distribution with an eccentric source for human bladder optical properties.
van Staveren Keijzer H J[1], Keijzer M, Keesmaat T, Jansen H, Kirkel W J, Beek J F, Star W M. http://iopscience.iop.org/article/10.1088/0031-9155/41/4/001/meta If there is bladder cancer, then there will be diseased tissue and as a result bladder lesions will absorb more light than healthy bladder tissue at some of the potential treatment wavelengths, providing variations in the amount of light absorbed by any particular bladder wall surface area.

If the light emitter moves during the above procedure and touches the bladder wall for any length of time, it is possible that the light emitter will cause irreparable thermal damage to the bladder wall, due to the high emission powers needed in order to achieve a PDT efficacy. Such damage will certainly affect safety and tolerability of the procedure.

In an exemplary embodiment of the present invention, a fiber-optic cage is placed in a device such as a cystoscope. The cystoscope enters the bladder, and the cage is deployed like an umbrella (or similar to inflating a football); therefore detecting different amounts of light within various areas of the bladder. The fiber-optic cage desirably includes twelve (12) to sixteen (16) light detectors depending on the size of the bladder wall surface, the required spatial resolution of the irradiance, fluence or fluence rate on the bladder wall surface (although more or less may be included). The light detectors are situated so that they detect light from respectively different areas of the bladder. The values obtained from each respective light detector can then be looked at and evaluated by being displayed in a form such as a histogram or bar chart. In this manner, a urn-oncologist is able to identify several issues: 1) if data from one sensor indicates a value greater than data from other sensors, this can indicate that the fiber optic is too close to the bladder wall and possibly touching the bladder wall; 2) the data may indicate that the light emitter needs to be adjusted so that it is more at the geometric center of the bladder regardless of shape or size; and 3) the data may indicate that not enough light is reaching one area of the bladder wall and therefore activation of the drug at that location may be minimal or not occur at all. As a result of obtaining all this information, it is possible to deliver a more homogeneous amount of light throughout the bladder and therefore achieve more homogeneous activation of the PS.

The above described use within the bladder is merely exemplary. It is understood that the present invention can be implemented within other body cavities and/or other types of organs, such as the lungs or brain.

DETAILED DESCRIPTION

The Canadian Cancer Society estimates that 7,900 people in Canada will be diagnosed with bladder cancer this year, making it the 5$^{th}$ most common cancer in Canada (4$^{th}$ most common among men, with 5,900 cases and 12$^{th}$ most common among women with 2,000 cases).

With a recurrence rate of nearly 80%, bladder cancer is the most expensive cancer to treat on a per patient basis. The high recurrence rate raises many issues affecting quality of life because of its persistence.

The Canadian Urology Association Journal issued a guideline for the treatment of NMIBC in 2010. This guideline provides a Canadian consensus on the management of NMIBC. According to this guideline, the Transurethral Resection of Bladder Tumor ("TURBT") procedure is the first-line and gold standard treatment for NMIBC.

Intravesical therapy can be either chemotherapy or immunotherapy and is either therapeutic, prophylactic or adjuvant in the immediate postoperative setting.

Treatment options for recurrent bladder cancers are limited and often consist of systemic chemotherapy combined with or without a radical cystectomy. A radical cystectomy is the removal of the entire bladder, nearby lymph nodes, part of the urethra, and nearby organs that may contain cancer cells. In men, the prostate, the seminal vesicles, and part of the vas deferens are also removed. In women, the cervix, the uterus, the ovaries, the fallopian tubes, and part of the vagina are also removed.

Intravesical therapy for patients with superficial papillary bladder cancer at risk for tumor recurrence appears reasonable, provided the therapy requires a limited number of treatments to be delivered, causes minimal toxicity to the patient and can delay recurrence for a reasonable length of time. Other active agents with a more favorable safety profile than Bacillus Calmette-Guerin ("BCG") need to be identified for prophylactic use in this patient population. Prevention of superficial recurrences is important as it would spare the patient further urinary symptoms and repeated TURBT procedures and the potential risk with associated complications and mortality, particularly in older patients, as well as to decrease the requirement for quarterly cystoscopic follow-up and the anxiety associated with discovery of new tumor growths.

PDT is a promising strategy for treating cancer; whereby, light is used to activate an otherwise nontoxic PS in order to destroy tumors and tumor vasculature and to induce an immune response. Following photoactivation, the PS delivers a toxic burst of cytotoxic singlet oxygen and other Reactive Oxygen Species ("ROS") that are confined spatially and temporally to the irradiated region, thus targeting malignant tissue while sparing healthy tissue.

Although PDT technology has been known for many years, the use of PDT for cancer treatment has been limited. For example, a large number of variables may need to be optimized in certain situations, making the development of such therapies more challenging (i.e. PS, dose of PS light source, wavelength, light dose, drug-to-light interval between application, dosimetry, and protocol design) for each clinical application.

PSs can be employed in PDT mediated treatment of various cancers including human bladder carcinoma. PSs selected for bladder cancer should have properties that increase the safety and efficacy of the PS for use in bladder carcinoma PDT:
  Able to be delivered effectively to the target tissue
  Exceptional resistance to photobleaching (allows efficacy over longer treatment times without the need for reapplication)
  Singlet oxygen quantum yield near unity (very efficient conversion of light photons into singlet oxygen)
  Drive both Type I and Type II processes (a powerful and versatile PS in oxygen rich or poor environments)

While the following description describes the use of TLD-1433, TLD-1433 is merely exemplary, and it is understood that other PSs may be used in place of TLD-1433.

As explained in the Overview, and further described below, cage 200 will be deployed in an organ, such as a bladder, in order to measure light exposure at a plurality of locations within the organ. It is thus desirable to know the internal volume of the organ. This may serve several purposes. First, it is desirable to know how much TLD-1433 is to be instilled into the organ. Second, it is desirable to know a preferential dimension(s) to be chosen for cage 200. A solution such as distilled water can be used to fill the organ until backpressure suggest to the physician that the bladder folds are removed or bladder unfolding has been verified by ultrasound. In the case of a bladder, exemplary bladder volumes, cage dimensions, power delivery, catheter sizes and detector locations are as follows:

| Volume (ml) | Radius (cm) | Surface Area (cm2) | Arm Length (cm) | Power Delivered Low albedo (mW) | Power Delivered High albedo (mW) |
|---|---|---|---|---|---|
| 150 | 3.3 | 136.5 | 10.4 | 2275 | 758 |
| 175 | 3.5 | 151.3 | 10.9 | 2521 | 840 |
| 200 | 3.6 | 165.4 | 11.4 | 2756 | 919 |
| 225 | 3.8 | 178.9 | 11.9 | 2981 | 994 |
| 250 | 3.9 | 191.9 | 12.3 | 3000 | 1066 |
| 275 | 4.0 | 204.5 | 12.7 | 3000 | 1136 |
| 300 | 4.2 | 216.7 | 13.0 | 3000 | 1204 |
| 325 | 4.3 | 228.6 | 13.4 | 3000 | 1270 |
| 350 | 4.4 | 240.2 | 13.7 | 3000 | 1334 |
| 375 | 4.5 | 251.5 | 14.1 | 3000 | 1397 |
| 400 | 4.6 | 262.5 | 14.4 | 3000 | 1458 |
| 425 | 4.7 | 273.4 | 14.7 | 3000 | 1519 |
| 450 | 4.8 | 284.0 | 14.9 | 3000 | 1578 |
| 475 | 4.8 | 294.4 | 15.2 | 3000 | 1635 |
| 500 | 4.9 | 304.6 | 15.5 | 3000 | 1692 |
| 525 | 5.0 | 314.7 | 15.7 | 3000 | 1748 |
| 550 | 5.1 | 324.6 | 16.0 | 3000 | 1803 |
| 575 | 5.2 | 334.4 | 16.2 | 3000 | 1858 |
| 600 | 5.2 | 344.0 | 16.4 | 3000 | 1911 |

The resulting three catheter sizes are:
TLC-3410S is for bladder volumes from 135-264 ml and detectors at 2.5 cm, 5 cm, 7.5 cm, 10 cm from the bladder dome
TLC-3420M is for bladder volumes from 233-456 ml and detectors at 3 cm, 6 cm, 9 cm, 12 cm from the bladder dome
TLC-3430L is for bladder volumes from 370-724 and detectors at 3.5 cm, 7 cm, 10.5 cm, 14 cm from the bladder dome The target light delivery interval delivers a set fluence, fluence rate or irradiance to the target tissue. Said target irradiance includes the primary irradiance delivered by the isotropic emitter and the diffuse reflectance from all bladder segments. The latter contribute to the M-factor of the bladder which acts as an integrating sphere. M-factors for the bladder have been reported to range from 2 to 6, with the lower M factor equivalent to a low albedo case with extensive disease and little to none "normally white appearing" bladder wall; whereas, high M factors are for high quantities of "normally white appearing" bladder wall with little distention The last two columns in the table list the initial power setting for the laser to deliver the desired optical dose of 90 Jcm-2 for the low and the high albedo case. As the maximum power output of the system is 3 W, for the low albedo case the target light delivery may not be attained, within 45 minutes thus at the maximum power setting the illumination time will be required to be extended.

Prior to use, the treatment power settings for emitter fiber 305 (and emitter 325) are verified. In one exemplary embodiment of the present invention, a closed container that is referred to as an integrating sphere may be used. The integrating sphere may be filled, for example, with 100 milliliters ("ml") of sterile USP water. Emitter fiber is inserted through the top aperture of the integrating sphere after removal of the cap and then activated. The integrating sphere detects the actual emitted optical power of the emitter fiber. The resulting signal is measured, where it is translated in to Watts ("W") and displayed. Calibration may also occur by inserting emitter fiber 305 into a transparent calibrating sleeve prior to insertion into the integrating sphere.

TLD-1433 may be supplied in a borosilicate vial and subsequently reconstituted. Depending on the high or low target dose, desirable concentration of TLD-1433 may be achieved depending upon the patient's bladder volume. An appropriate volume of sterile water may be added to achieve a clinical dilution of 0.35 mg/cm2 or 0.70 mg/cm2. The final solution may be instilled in the bladder cavity for sixty (60) minutes. Any surface bound photosensitizer is removed by flushing the bladder three times with sterile water. The bladder is desirably distended during the third flush to try to prevent folds in the bladder wall that may prevent uniform light illumination.

A cystoscope with preferably a 4.5 mm (13.5 French) working channel is then placed through the urethra to the bladder neck. Cage 200 is then introduced into the bladder as more clearly described below.

Figure 1:
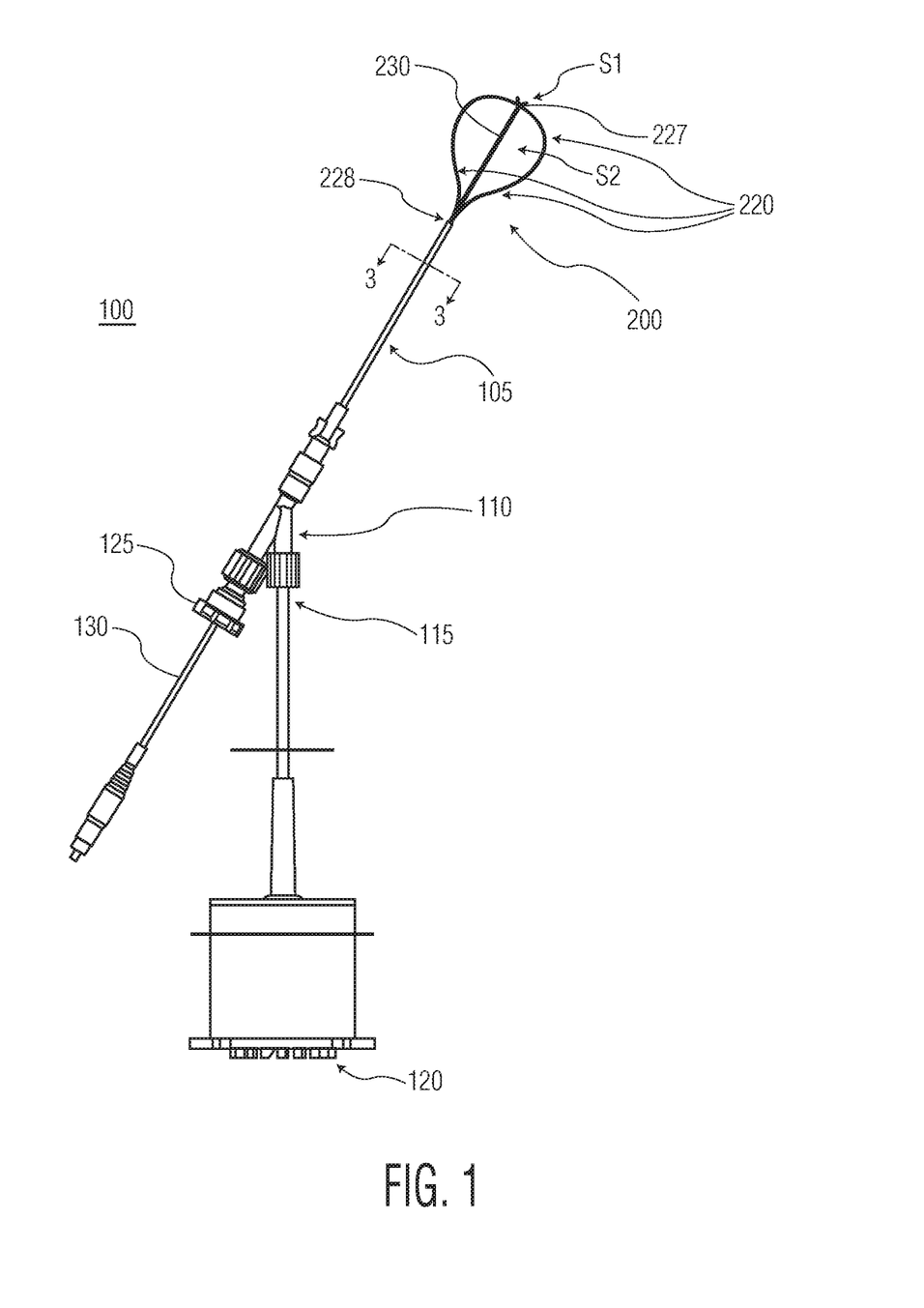
FIG. 1 is a line drawing that illustrates a probe in accordance with an exemplary embodiment of the present invention.
Figure 4A:
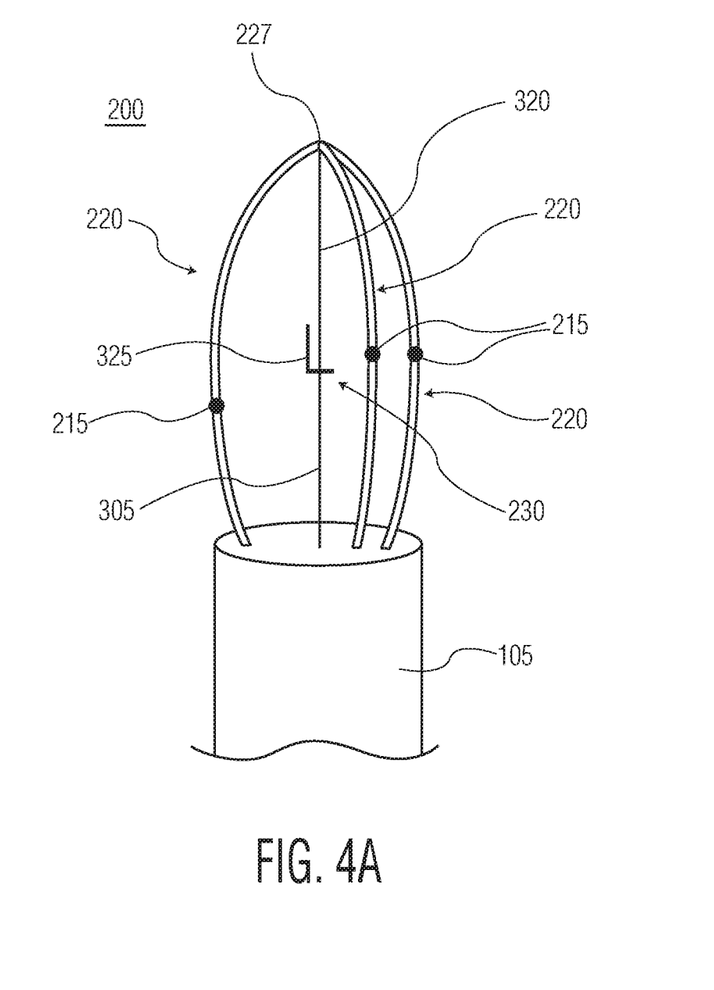
FIG. 4A illustrates the relative location of sensors and/or detectors situated along optical fibers extending from an arm in a perspective view in accordance with an exemplary embodiment of the present invention.
Figure 4B:
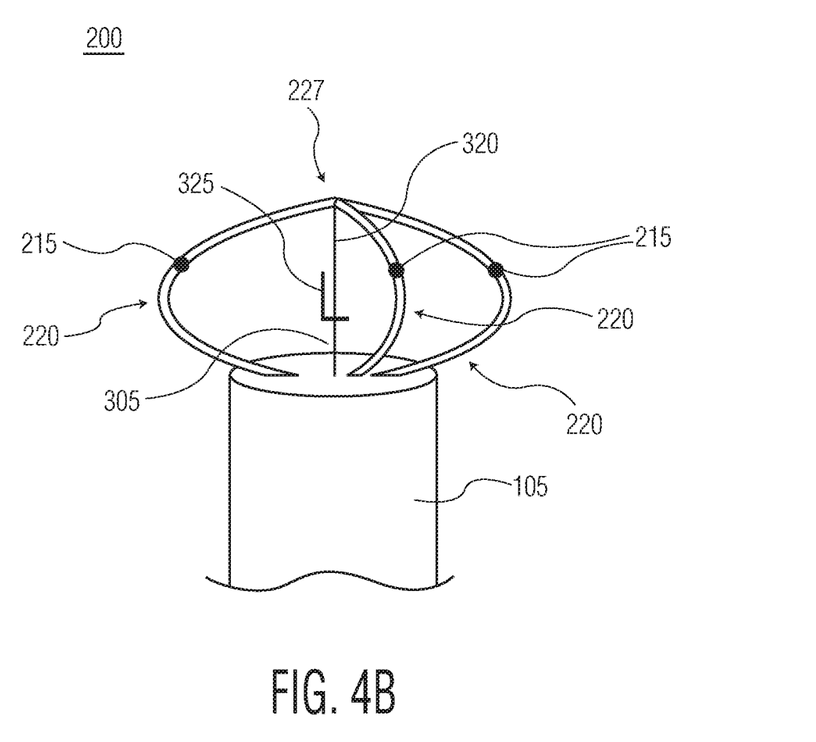
FIG. 4B illustrates the optical fibers extending from an arm in an expanded state compared with the configuration of optical fiber shown in FIG. 4A.

FIGS. 1, 4A and 4B illustrate a probe in accordance with an exemplary embodiment of the present invention. Probe 100 includes main shaft 105, in an exemplary embodiment of the present invention, main shaft 105 is a cystoscope that may be used for introducing cage 200 into the bladder. Cystoscopes are well known in the art. An exemplary cystoscope is a Karl Storz Hopkins II Telescope 4 mm/30 degree cystoscope (Model #27026DA). Further exemplary cystoscopes are manufactured by Olympus. Protruding from a top end of the cystoscope is cage 200. Cage 200 includes a plurality of fiber strands (or fiber portions) 210 (more clearly shown in FIG. 2). The fiber strands are desirably separated into three groups of four strands each so that three arms 220 are formed. The three arms 220 all merge near the top of cage 200 at apex 227. The three arms 220 all merge near the bottom of cage 200 at neck 228. Neck 228 is shown in FIG. 1 as being at the end of main shaft 105, i.e. at the location where arms 220 exit main shaft 105, but it is understood that neck 228 may be situated as other locations away from main shaft 105 as well.

The above explanation refers to "fiber strands" but a single fiber with multiple fiber portions may also be used to form cage 200.

When the word "cage" is being used, what is meant is a three dimensional space that is defined by a plurality of fibers. The fibers are situated so that they can bend and thus vary at least one dimension of the three dimensional space. The at least one dimension varied may result in the cage expanding outward or bulging as more fully described below. The outward expansion or bulging may be accompanied by a simultaneous reduction in dimension of the cage from an apex to a bottom thereof. Again, this motion is further described below and illustrated in the accompanying drawings.

Cage 200 may be a 3.3 mm outer diameter assembly comprising, for example 12×250 micron light sensors and an 850 micron light delivery sphere. The twelve light sensors are assembled in three linear arrays (arms 220) with four detectors 215 each. The three arms 220 cover the bladder wall surface separated by 120 degrees of longitude. Upon insertion, the three arms surround emitter 325 (shown in FIGS. 4A and 4B). Upon placement in the bladder, arms 220 are adjusted to resemble a hemispherical shape in a manner so that detectors 215 (covered by a medical grade heat shrink tubing, ie. an industry-standard polyethylene material) are abutting the bladder wall surface. The arms may be fixed at apex 227 and at the opening of main shaft 105 using a fitting made from polyether ether ketone ("PEK") plastic, while other materials may also be suitable.

Cage 200 also includes central member 230 is also included. Central member 230 may be moved within main shaft 105 via motion from rod 130. Thus, as rod 130 is moved up within shaft 105, central member 230 also moves up. Furthermore, while rod 130 moves down, central member 230 moves down.

Central member 230 moves up and down. The motion of central member 230 can be independent from the motion of arms 220 into and out of main shaft 105. Thus, as more clearly explained below, if central member 230 is drawn into main shaft 105, sensors located on arms 220 will move away from each other. Furthermore, as central member 230 extends further out of main shaft 105, sensors located on arms 220 will move towards each other. This motion is more clearly described below.

Probe 100 includes lock 125. When lock 125 is actuated, central member 230 is prevented from moving independently of arms 220. Thus, loosening lock 125 allows rod 130 to move in and out, thus causing central member 232 to move in and out of main shaft 105, thus in turn causing detectors situated on arms 220 to move towards and away from each other. Again, there are other ways to describe this motion as explained below. The fiber strands that comprise arms 220 extend downward into main shaft 105 and into probe tube 115 before terminating at connectors 120. Appropriate electronics may then be connected to connectors 120 no that it is possible to measure the amount of light that is striking each detector 215 situated on each fiber strand 210.

Probe tube 115 is connected to main shaft 105 via Y-connector 110. In this manner, movement of central member 230 may be controlled by moving rod 130 in and out.

Figure 2A:
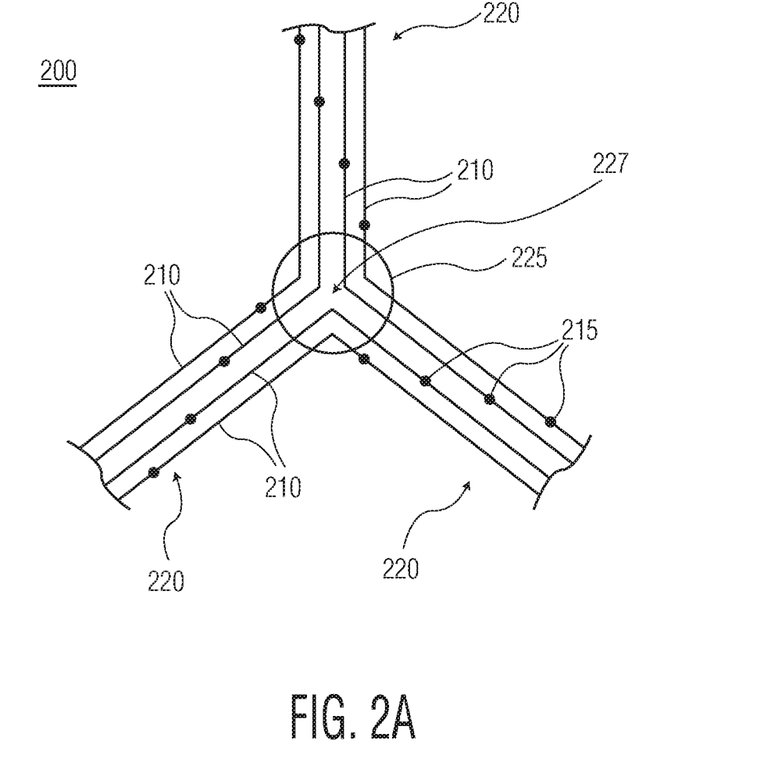
FIG. 2A illustrates the orientation of optical fibers relative to each other in a line drawing in accordance with an exemplary embodiment of the present invention.
Figure 2B:
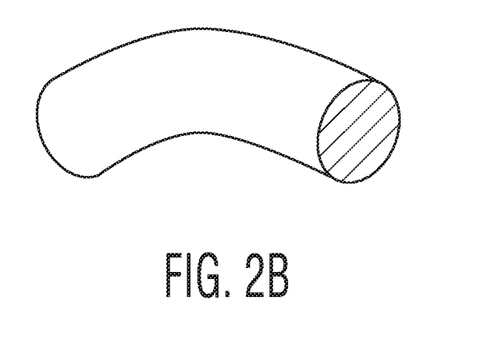
FIG. 2B-2G are various embodiments of light sensors incorporated in an optical fiber.

FIG. 2A illustrates a portion of cage 200 before it is inserted into main shaft 105. As shown, cage 200 is comprised of six fiber strands 210 which each include a bend in a central portion thereof. The bend within each fiber strand 210 terminates at apex 227. Furthermore, suture 225 is placed around apex 227 in order to maintain all of the fiber strands 210 together at apex 227. Along each portion of fiber strand 210 that descends from apex 227 into main shaft 105, a respective detector 215 is formed. Each detector is coupled to appropriate electronics for measuring the amount of light entering each detector 215.

Each fiber strand 210 is cut to an appropriate size in order to form desired dimensions for cage 200. In one exemplary embodiment of the present invention, the fiber strands may be comprised of six 6.2 m long 250 micrometer POE. While fiber strands are well known in the art, an exemplary fiber strand is Mitsubishi Rayon Super Eska SK-10. This is a high performance plastic optical fiber, although other optical fibers may also be used.

Detectors 215 are formed into fiber strands 210 as follows. At an appropriate location along each fiber, a plurality of ablation cuts may be performed using a heating element. Each fiber may be ablated close to half way through. At each ablation location, scattering material may be filled in to create a detector. The scattering material may include 2 parts resin, one part hardner, mixed for example with twice the weight of barium sulfate and combined. Using a needle, the epoxy can be applied to the ablated hole. In this manner, detectors 215 are formed in fiber strands 210.

The fiber strands are then oriented as shown in FIG. 2A. FIG. 2A illustrates the manner in which fiber strands 210 are placed relative to each other. The location where the fiber strands 210 bend will become apex 227. Around the area which will be designated as apex 227, suture 225 is placed. Furthermore, fiber strands 210 are grouped into three separate groups this forming three arms 220, each with four fiber strand portions and each with four detectors 215. The resulting arms 220 will then descend into main shaft 105. The three arms are oriented at approximately 120 degrees relative to each other.

Various embodiments of optical sensors that are integrated in the optical fibers are possible. Reference is made to FIGS. 2B-2G, Optical fibers are multimode silica or plastic optical fibers preferably with a high NA to achieve good sensitivity. These include:

A bare length of fiber where in the fiber end is polished roughly as shown in F which is detecting light predominantly along the axis of the optical fiber.

Figure 2C:
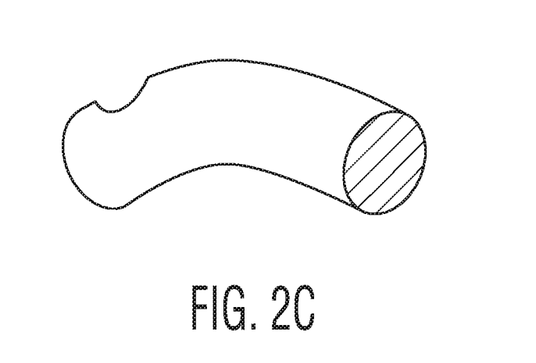

A polished fiber with a section cut out of it as shown in FIG. 2C. The fiber is cut with a scalpel as illustrated in 3c, with the first cut peeling back a section of the core and cladding, resulting in a fiber with an acceptance angle approximating 2 Pi sterad, albeit with unknown azimuth and polar angle dependence. (cut can also be achieved using thermal denaturation for plastic optical fibers.

Figure 2D:
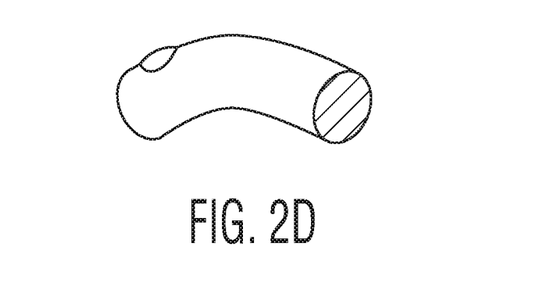

FIG. 2D, a cut fiber as in FIG. 2C has the cut filled in with epoxy. The epoxy can includes barium sulfate or other diffusing materials. In a further embodiment, a cut fiber has the notch filled with just epoxy (no barium sulfate), resulting in a fiber with an acceptance angle approximating 2 Pi Sterad, albeit with homogenous azimuth and polar angle dependence.

Figure 2E:
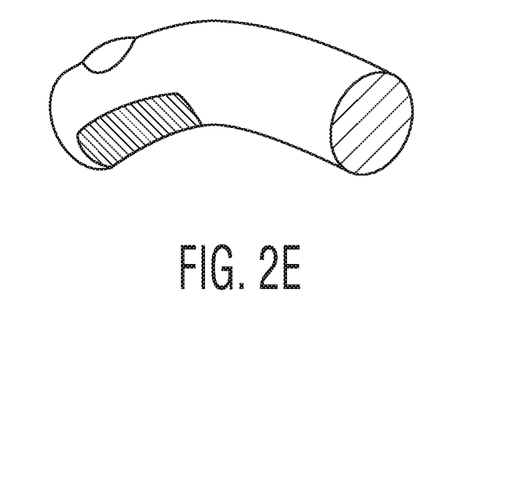

FIG. 2E shows an epoxy-filled fiber painted with black paint on the side opposite the cut along a small length of the fiber. The cut side of the fiber is then cleaned. The application of the paint is verified using a laser pointer at one end and ensuring that on one side, the laser light is visible and a 180° rotation causes the light to be blocked out entirely. This results in a sensor that is sensitive only to one hemisphere or Pi Sterad, and hence acts as an irradiance sensor.

Figure 2F:
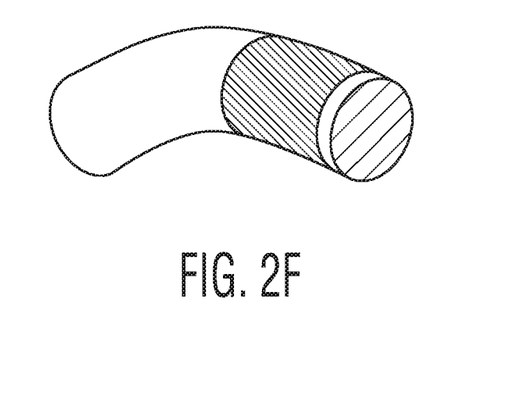

FIG. 2F shows a section of a polished (otherwise unmodified) fiber is painted with black paint.

Figure 2G:
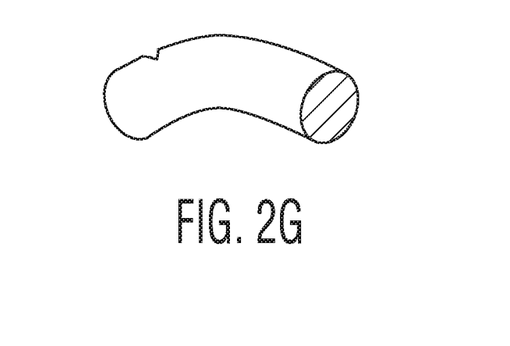

FIG. 2G shows a fiber with the notch cut by laser is polished roughly on one end. In a further embodiment, the notch is filled with epoxy as described above resulting in a 180° rotation causes the light to be blocked out entirely. This results in a sensor that is sensitive only to one hemisphere or Pi Sterad, and hence acts as an irradiance sensor.

Figure 3:
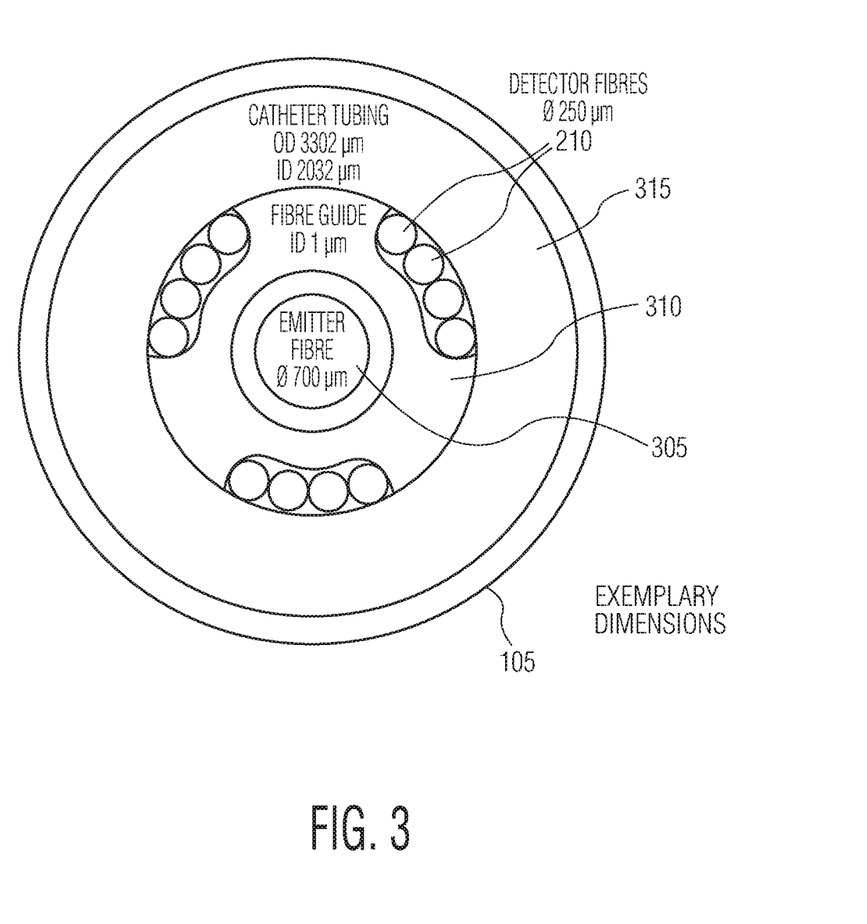
FIG. 3 is a cross-sectional view taken along cutline A-A shown in FIG. 1.

FIG. 3 is a cross-sectional view taken along section line A-A that appears in FIG. 1. Along the very outside is main shaft 105. Within main shaft 105 is catheter 315. Within catheter 315 is fiber guide 310. Between fiber guide 310 and catheter 315 is situated each fiber strand 210. Within fiber guide 310 is emitter fiber 305.

FIG. 4A and FIG. 4B illustrate how the distance between detectors 215 can be increased or decreased so that detectors 215 are able to be situated along the walls of the bladder. FIG. 4A illustrates how three arms 220 are extending out of main shaft 105 at approximately 120 degrees relative to each other. Further extending out of main shaft 105 is central member 230. Central member 230 is comprised of emitter fiber 305, emitter 325 from which light is emitted, and guide wire 320. The end of guide wire 320 is connected to apex 227. As shown in FIG. 4A various detectors 215 are shown. These detectors 215 are located a certain distance away from each other. The exemplary distance illustrated in FIG. 4A may correspond to one bladder shape. While there are a total of 12 detectors in the exemplary embodiment, only three detectors are shown in FIG. 4A for the sake of clarity. Looking now at FIG. 4B, detectors 215 are still shown. However, detectors 215 shown in FIG. 4B are further apart then detectors 215 shown in FIG. 4A. That is because guide wire 320 has been retracted into main shaft 105 without also retracting arms 220 into main shaft 105. Thus, as guide wire 320 retracts into main shaft 105, cage 200 effectively bulges outwards. In this manner, the configuration shown in FIG. 4B may be better suited for a bladder with a different size or shape in the bladder that may receive cage 200 with the configuration shown in FIG. 4A.

Furthermore, it is possible for guide wire 320 to extend out of main shaft 105, again without arms 220 also extending out of main shaft 105. In this manner, cage 200 shrinks inward, or in other words transitions from the shape shown in FIG. 4B to the shape shown in FIG. 4A. However, there are other ways to express this motion as described below.

When transitioning from the shape shown in FIG. 4A to the shape shown in FIG. 4B, cage is bulging, but the difference in cage 200 between the two figures can be described in other ways as well. For example, the motion causes detectors 215 situated along fiber strands 215 to move away from each other. The motion can be described as cage 200 opening outward (i.e.: the motion made by an umbrella when it opens). The motion can be described as cage 200 expanding along a plane. The motion can be described as cage 200 expanding along a plane in multiple directions. The plane can be described as perpendicular to guide wire 320. The motion can be described simply as expansion of cage 200. The motion can be described as cage 200 expanding while the distance from apex 227 to bottom 228 decreases.

To clarify, emitter fiber 305 extends from emitter 325, through main shaft 105, and is coupled to rod 130. The end of emitter fiber 305 is connected to apex 227 via guide wire 320. Thus, motion of rod 130 into and out of main shaft 105 causes cage 200 to expand and contract (which can be described in other ways as explained above). In one exemplary embodiment of the present invention, main shaft 105 is a cystoscope and guide wire 320 is sliding through a catheter within the cystoscope. This motion of rod 130 also enables a change in the location of emitter 325 relative to the sidewalk of the bladder. Thus, rod 130 can be moved until the (twelve) detectors 215 indicate that they are receiving substantially similar amounts of light (plus or minus an acceptable deviation). Once it can be verified that detectors 215 are receiving substantially similar amounts of light, the position of emitter 325 can then be locked in place for the duration of the procedure.

As cage 200 expands, detectors 215 will move closer to the bladder wall, and then either will be situated along the bladder wall, or sufficiently close thereto in order to measure the amount of light being received from emitter 325. It is desirable for detectors 215 to face towards the geometric center of the bladder and thus towards emitter 325. In this manner, detectors 215 are able to receive irradiance delivered to the bladder wall both by emitter 325 and scattered (laser) light from the bladder wall. In one exemplary embodiment of the present invention, close proximity of detectors 215 to the bladder wall is sufficient as irradiance inside an integrating sphere such as a a bladder may be homogenous.

Furthermore, cage 200 may be available in multiple sizes and/or with respectively different dimensions. Therefore, if the volume of the bladder is known prior to insertion of cage 200, the dimensions of cage 200 can be selected so that cage 200 when fully expanded touches or is sufficiently close to the bladder wall.

As previously explained, rod 130 may be moved in order to vary the location of emitter 325 within a bladder. In one exemplary embodiment of the present invention, linear motion of rod 130 may cause expansion (and alternatively contraction) of cage 200 while simultaneously causing the location of emitter 325 within the bladder to change. As previously explained, a surgeon may wish to change the location of emitter 325 within a bladder if all of the detectors 325 are not receiving a sufficiently similar amount of light. The surgeon will thus manipulate rod 130 to cause the location of emitter 325 to change. While the manipulation of rod 130 will also cause expansion/contraction of cage 200, the amount of expansion/contraction of cage 200 is relatively minor and does not (by itself) have an adverse affect on the ability of detectors to receive light from emitter 325.

It is understood that emitter 325 can have multiple forms, in a point emitter, a cylindrical emitter, a cut end fiber, etc.

In an alternative embodiment of the present invention, independent controls are provided for independent control of expansion/contraction of cage 200 and location of emitter 325, respectively.

Figure 5:
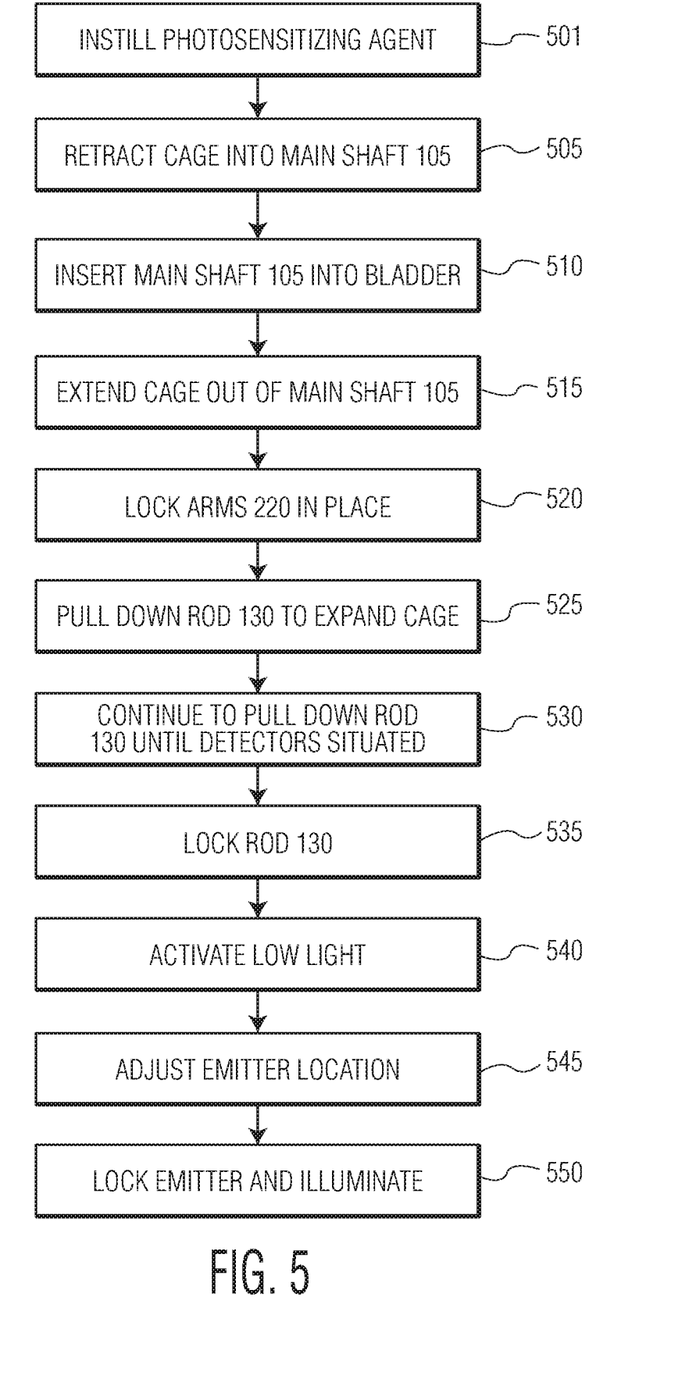
FIG. 5 is a flowchart diagram which illustrates a method in accordance with an exemplary embodiment of the present invention.

FIG. 5 is a flowchart diagram which illustrates the operation of the exemplary embodiment of the present invention. At optional step 501, after the volume of the bladder is measured (or approximated), the photosensitizing agent, TLD-1433, is instilled into the bladder cavity via the urethra. Instillation of TLD-1433 should be approximately 60 minutes. The bladder is then drained, optionally filled and drained with distilled water (perhaps multiple times), and then filled with distilled water again. At step 505, cage 200 is retracted into main shaft 105. At step 510, main shaft 105 is inserted into a bladder. At step 515, cage 200 is extended out of main shaft 105. At step 520, arms 220 are locked into place so they neither extend out of nor retract into main shaft 105. At step 525, lock 125 is actuated and rod 130 is pulled downward in order to expand cage 200. At step 530, rod 130 continues to be pulled down until detectors 215 situated on fiber strands 210 come into contact with (or are sufficiently close to) the bladder wall. At step 535, rod 130 is locked into position by actuating lock 125.

Figure 6:
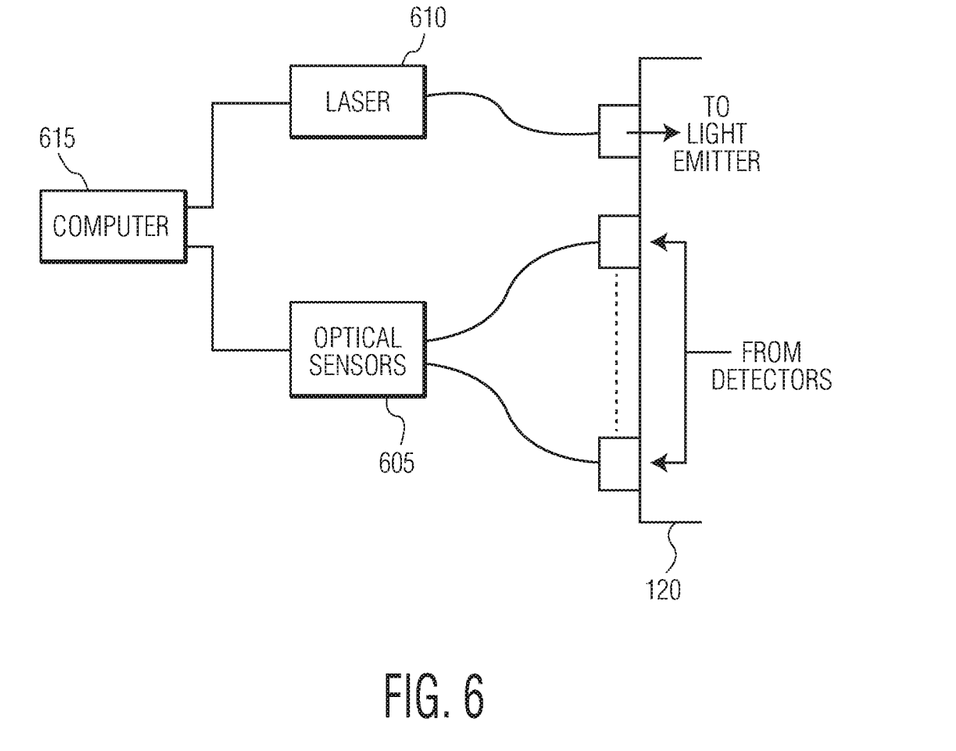
FIG. 6 is a block diagram that illustrates connections between a light emitter, a light source, detectors, sensors and computer(s) in accordance with an exemplary embodiment of the present invention.

At step 540, irradiation begins. Emitter 325 may comprise, for example, a spherical diffuser of 850 μm diameter that is mounted on emitter fiber 305 having a 400 μm core diameter (isotropy>±10%). Emitter fiber 305 may be connected to an external light source as illustrated in FIG. 6 and further described below. After optimum positioning of the light-emitting diffuser associated with emitter 325 (deviation from the mean fluence rate <10% across the whole bladder wall area is the desired target) the patient is ready to commence photo activation of the photosensitizer.

The target irradiance is 33.3 mWcm-2 with a target radiant exposure of 90 Jcm-2 to avoid tissue damage by PDT. Irradiation is at 525 nm for a target time of 45 minutes; however, information that is made available in accordance with an exemplary embodiment of the present invention is desirably considered when deciding at what time the irradiance is completed.

For optimization purposes, upon inserting cage 200 into the bladder, a source such as a laser is switched on at a setup power (10% of target power) and irradiance readings are obtained and displayed on a screen. At step 545, the position of emitter 325 within the bladder is manipulated until all twelve detectors 215 indicate irradiance readings are within a threshold, such as ±10% relative to each other. An audible alarm may also be sounded when the readings are within the threshold.

At step 550, radiant exposure readings (Jcm)-2 at the twelve sensor locations may be displayed on a screen. The light source (e.g. laser) is then switched to a target power and operation is commenced. In one exemplary embodiment of the present invention, irradiance measurements are collected every five to ten seconds and the radiant exposure is integrated over this time, providing a physician with a graphical representation of the accumulated radiant exposure at each of the twelve detectors 215 since the treatment has commenced. In one exemplary embodiment, three horizontal lines are displayed representing: i) Target Dose (90 Jcm-2); ii) Min. Dose (81 Jcm-2); iii) Max. Dose (99 Jcm-2).

In a further exemplary embodiment of the present invention, the ongoing irradiance can be monitored and a prediction can be made as to when the target±10% irradiance in all areas monitored by detectors 215 is attained based on the current position of the light source. If the prediction is unsatisfactory, the surgeon has the option to return to the low power option to further adjust the position of emitter 325 and retry the treatment to adjust for equal light delivery.

After the desirable amount of time has elapsed, emitter 325 is turned off, cage 200 is retracted into main shaft 105, and main shaft 105 is retracted from the bladder.

FIG. 6 is a block diagram which illustrates connection of various components in accordance with an exemplary embodiment of the present invention. As illustrated in FIG. 1, connectors 120 are included for providing connection to detectors 215 and emitter 325. As light is captured by detectors 215, the light is transmitted through fiber strands 210 until reaching connector 120. From connector 120, the signals may be transmitted to optical sensors 605. Optical sensors 605 measure magnitude of the light signals that have been received by detectors 215. The magnitude of the light signals received by detectors 215 is then stored in computer 615. Furthermore, a light source such as laser 610 may be included. Light source 610 may provide a source of light which is transmitted via a further fiber strand 210 until reaching and then being emitted by emitter 325.

Figure 7A:
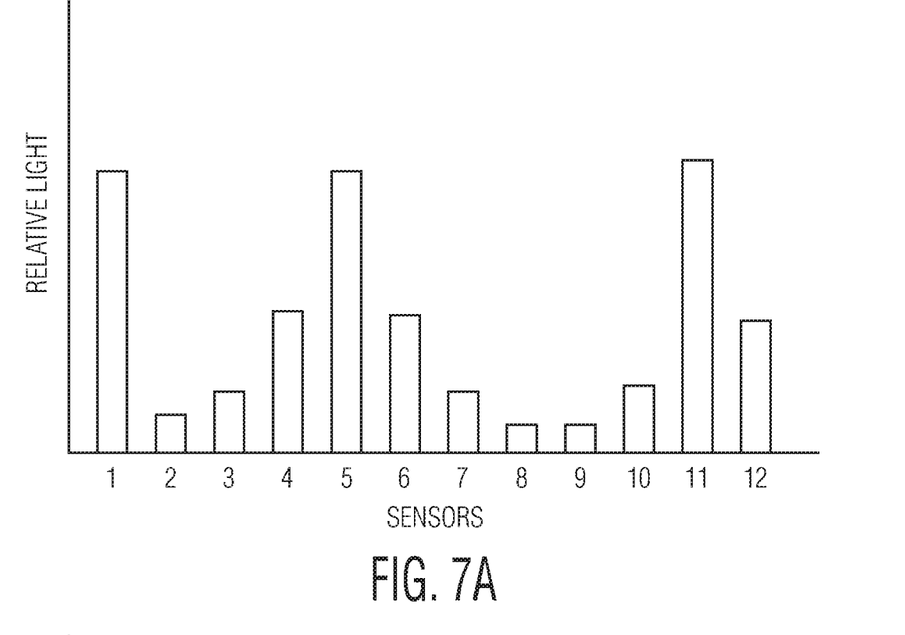
FIG. 7A and FIG. 7B are bar graphs that illustrate exemplary data that is obtained by performing data acquisition in accordance with an exemplary embodiment of the present invention.
Figure 7B:
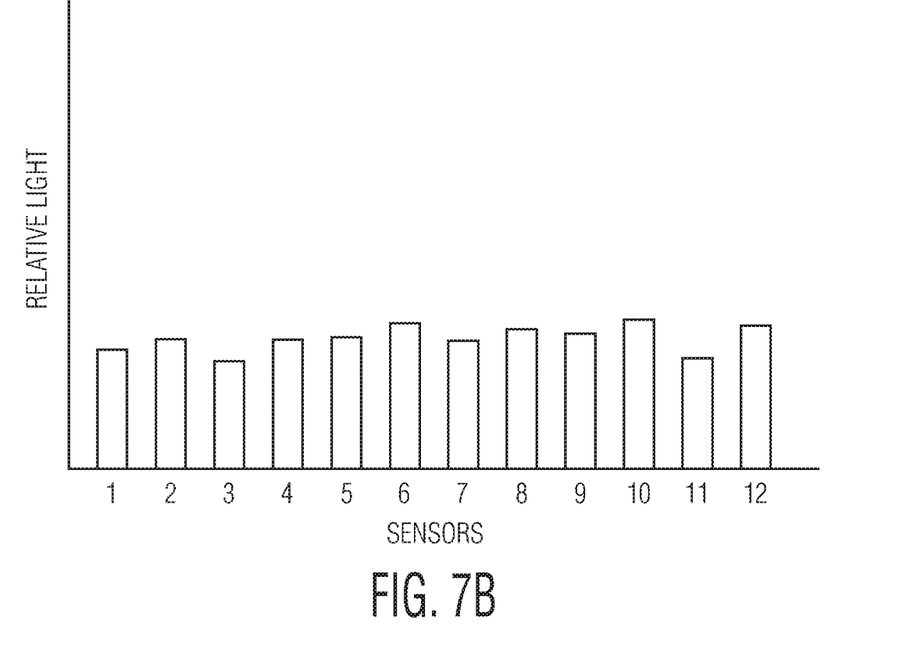

As previously explained, depending upon numerous factors such as the location of emitter 325 within the bladder, the size of the bladder, the shape of the bladder, the existence of cancer within the bladder, etc., the magnitude of light received by each of the detectors 215 may be very different. After the magnitude of light received by each of the detectors 215 is stored in computer 615, computer 615 may generate a visual display which allows a surgeon to understand the relative amount of light being received by each of the detectors 215. FIG. 7A illustrates one such visual display. As shown in FIG. 7A, sensors 15 and 11 are receiving much more light than average, while sensors 2, 8 and 9 are receiving much less light than average. After seeing the visual display that is exemplified in FIG. 7A, the surgeon may change the location of emitter 325 within the bladder. After changing the location of emitter 325 within the bladder, the surgeon may then view a further visual display of the relative magnitude of light being received by all of the sensors. A further exemplary visual display is illustrated in FIG. 7B. As shown in FIG. 7B, the average magnitude of light being received by all of the sensors is substantially the same. In one exemplary embodiment of the present invention, the magnitude of light received by each of the detectors 215 may not be exactly equal, but may be sufficiently close so that subsequent irradiation and activation of the photodynamic drug may occur. In any event, once a surgeon sees from a visual display that the relative magnitude of light received by each of the detectors 215 is sufficiently close, light source 610 may be energized to provide a sufficient amount of light for activation of the photodynamic drug, and the light may remain at that level for a sufficient time period, e.g. one hour.

While the present invention has been described herein with reference to exemplary embodiments, it should be understood that the invention is not limited thereto. Those skilled in the art with an access to the teachings herein will recognize additional modifications, applications, and embodiments within the scope thereof and additional fields in which the invention would be useful.

Embodiments of the invention also may be directed to computer program products comprising software stored on any computer useable medium. Such software, when executed in one or more data processing device, causes a data processing device(s) to operate as described herein. Embodiments of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnotogical storage device, etc.).

The present application has set forth one or more but not all exemplary embodiments of the present invention as contemplated by the inventor(s), and thus, is not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein, it is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An apparatus for illuminating, comprising:
a plurality of fibers that are separated into a plurality of groups, said plurality of fibers including fiber portions meeting at an apex and a bottom location to form a three-dimensional cage;
at least one optical sensor integrated in each of the fiber portions for receiving light and transmitting the light along each of the fiber portions, respectively; and
an illumination member situated on a central member within a three-dimensional space defined by the plurality of fibers of the cage,
wherein the at least one optical sensor comprises a notched section of the fiber portions from which an amount of cladding and core have been removed such that the at least one optical sensor has an acceptance angle of 1-2 Pi sterad.

2. The apparatus according to claim 1, further comprising a hollow shaft, wherein the fiber portions extend from the bottom location into the hollow shaft.

3. The apparatus according to claim 2, wherein the central member extends from the fiber portions to within the hollow shaft, and retracts into the hollow shaft without the fiber portions also retracting into the hollow shaft.

4. The apparatus according to claim 3, wherein the retraction of the central member into the shaft expands the cage.

5. The apparatus according to claim 1, wherein the cage is expandable in at least one dimension.

6. The apparatus according to claim 1, wherein at least a portion of each of the fiber portions is comprised of optical fiber.

7. The apparatus according to claim 1, wherein the illumination member comprises a spherical diffuser having a diameter greater than a diameter of the central member.

8. A method for illuminating a hollow member; the method comprising the steps of:
providing the apparatus of claim 1;
inserting the apparatus into the hollow member;
permitting light to emit from within the three-dimensional cage and towards the fiber portions;
receiving a reflected light at distinct locations on said fibers; and
allowing the fibers to transmit the reflected light received on each of the fiber portions out of the hollow member.

9. The method according to claim 8, further comprising a step of inserting a hollow shaft into the hollow member, wherein the fibers extend from an end of the hollow shaft.

10. The method according to claim 9, wherein the central member extends from the hollow shaft to the fibers, further comprising a step of retracting the central member into the hollow shaft without also retracting the fibers into the shaft.

11. The method according to claim 10, wherein the retraction of the central member into the shaft expands the cage in one dimension.

12. The method according to claim 10, wherein the light is emitted from the illumination member attached to the central member.

13. The method according to claim 8, wherein at least a portion of each of the fiber portions is comprised of optical fiber.

14. The method according to claim 8, further comprising a step of expanding the cage in at east one direction.

15. The method according to claim 8, further comprising a step of displaying relative amounts of light received at each of the distinct locations.

16. The method according to claim 8, further comprising a step of providing photosensitive medication into the hollow member before inserting the apparatus into the hollow member.

17. The method according to claim 16, wherein the hollow member is a bladder.

18. A method of performing a photochemical reaction n a hollow member, the method comprising the steps of:
a) inserting a photochemical that causes the photochemical reaction into the hollow member;
b) inserting the apparatus of claim 1 into the hollow member;
c) illuminating the hollow member from an illumination location within the hollow member;
d) receiving a reflected illumination from multiple locations about the illumination location;
e) changing the illumination location; and
f) maintaining the illuminating for a period of time.

19. The method according to claim 18, wherein step e) is preceded by a step of comparing the reflected illumination received from the multiple locations.

* * * * *